United States Patent
Lee et al.

[11] Patent Number: 5,679,828
[45] Date of Patent: Oct. 21, 1997

[54] BETULINIC ACID AND DIHYDROBETULINIC ACID DERIVATIVES AND USES THEREFOR

[75] Inventors: Kuo-Hsiung Lee, Chapel Hill, N.C.; Yoshiki Kashiwada, Niigata; Fumio Hashimoto, Kumamoto, both of Japan; Louis Mark Cosentino, Springfield, Va.; Mark Manak, Laurel, Md.

[73] Assignees: Biotech Research Labs, Inc., Rockville, Md.; University of North Carolina at Chapel Hill, Chapel Hill, N.C.

[21] Appl. No.: 463,071

[22] Filed: Jun. 5, 1995

[51] Int. Cl.$^6$ .................... C07C 69/753; A61K 31/505; A61K 31/52; A61K 31/215
[52] U.S. Cl. .................. 560/116; 560/194; 514/120; 514/253; 514/258; 514/418; 514/510
[58] Field of Search ............... 560/116, 194; 514/510, 120, 253, 258, 418

[56] References Cited

U.S. PATENT DOCUMENTS 5,468,888  11/1995  Bouboutou et al. ............... 554/58

FOREIGN PATENT DOCUMENTS 1415601  11/1975  United Kingdom.
WO 95/04526  2/1995  WIPO ............... A61K 31/00

OTHER PUBLICATIONS

Fujioka et al., Betulinic Acid and Platanic Acid as Anti-HIV Principles from *Syzigium claviflorum*, and the Anti-HIV Activity of Structurally Related Triterpenoids, *J. Natural Products* 57(2):243–247 (1994).
Fujioka et al. "Anti-AIDS agents, 11. Betulinic acid and platanic acid as anti-HIV principles from syzigium claviflorum, and the anti-HIV activity of structurally related triterpenoids". J. Natural Products, vol. 57(2): 243–247, 1994.
Klinor et al. "Triterpenes. XXI. 3,4-seco derivatives of betulinic acid". Collect. Czech. Chem. Commun. vol. 37(2): 603–609, 1972.
Mayaux et al. "Triterpene derivatives that block entry of human immunodeficiency virus type 1 into cells". Proc. Natl. Acad. Sci. vol. 91(9): 3564–3568, 1994.

Primary Examiner—José G. Dees
Assistant Examiner—Barbara Badio
Attorney, Agent, or Firm—Sterne, Kessler, Goldstein & Fox P.L.L.C.

[57] ABSTRACT

Some betulinic acid and dihydrobetulinic acid acyl derivatives according to the present invention have been found to have potent anti-HIV activity. Introducing a $C_2$–$C_{20}$ substituted or unsubstituted acyl group at the $C_3$-hydroxy group of betulinic acid and dihydrobetulinic acid produces the corresponding 3-O-acyl derivatives. The compounds of the present invention have the following formulae:

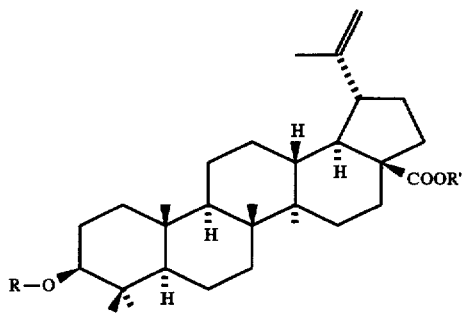

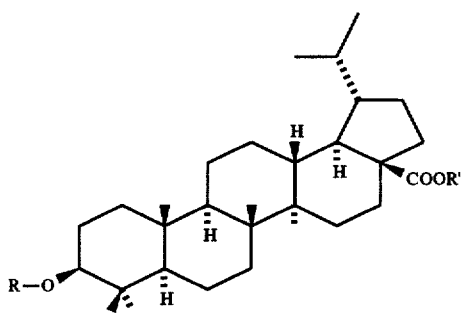

where R may be a mono- or dicarboxylacyl group, substituted or unsubstituted, of from about 2 to about 20 carbon atoms, and R' may be hydrogen or a $C_2$–$C_{10}$ substituted and unsubstituted alkyl or aryl group.

12 Claims, No Drawings

BETULINIC ACID AND DIHYDROBETULINIC ACID DERIVATIVES AND USES THEREFOR

Part of the work performed during development of this invention utilized U.S. Government funds under grant RO1-AI33066, awarded by the National Institutes of Health. The U.S. Government has certain rights in this invention.

FIELD OF THE INVENTION

The present invention relates to betulinic acid and dihydrobetulinic acid and derivatives thereof and their use as pharmaceuticals.

BACKGROUND OF THE INVENTION

Retroviruses

Retroviruses are small, single-stranded positive-sense RNA viruses. A retroviral particle comprises two identical single-stranded positive sense RNA molecules. Their genome contains, among other things, the sequence of the RNA-dependent DNA polymerase, also known as reverse transcriptase. Many molecules of reverse transcriptase are found in close association with the genomic RNA in the mature viral particles. Upon entering a cell, this reverse transcriptase produces a double-stranded DNA copy of the viral genome, which is then inserted into the chromatin of a host cell. Once inserted, the viral sequence is called a provirus. Retroviral integration is directly dependent upon viral proteins. Linear viral DNA termini (the LTRs) are the immediate precursors to the integrated proviral DNA. There is a characteristic duplication of short stretches of the host's DNA at the site of integration.

Progeny viral genomes and mRNAs are transcribed from the inserted proviral sequence by host cell RNA polymerase in response to transcriptional, regulatory signals in the terminal regions of the proviral sequence, the long terminal repeats, or LTRs. The host cell's protein production machinery is used to produce viral proteins, many of which are inactive until processed by virally encoded proteases. Typically, progeny viral particles bud from the cell surface in a non-lytic manner. Retroviral infection does not necessarily interfere with the normal life cycle of an infected cell or organism. However, neither is it always benign with respect to the host organism. While most classes of DNA viruses can be implicated in tumorigenesis, retroviruses are the only taxonomic group of RNA viruses that are oncogenic. Various retroviruses, such as the Human Immunodeficiency Virus (HIV), which is the etiological agent responsible for acquired immune deficiency syndrome (AIDS) in humans, are also responsible for several very unusual diseases of the immune system of higher animals.

HIV Infection and Aids

Human Immunodeficiency Virus (HIV) is a member of the lentiviruses, a subfamily of retroviruses. Many retroviruses are well-known carcinogens. HIV per se is not know to cause cancer in humans or other animals, but it does present a formidable challenge to the host. The viral genome contains many regulatory elements which allow the virus to control its rate of replication in both resting and dividing cells. Most importantly, HIV infects and invades cells of the immune system; it breaks down the body's immune system and renders the patient susceptible to opportunistic infections and neoplasms. The immune defect appears to be progressive and irreversible, with a high mortality rate that approaches 100% over several years.

HIV-1 is trophic and cytopathic for T4 lymphocytes, cells of the immune system which express the cell surface differentiation antigen CD4, also known as OKT4, T4 and leu3. The viral tropism is due to the interactions between the viral envelope glycoprotein, gp120, and the cell-surface CD4 molecules (Dalgleish et al., Nature 312:763–767, 1984). These interactions, not only mediate the infection of susceptible cells by HIV, but are also responsible for the virus-induced fusion of infected and uninfected T cells. This cell fusion results in the formation of giant multinucleated syncytia, cell death, and progressive depletion of CD4 cells in AIDS patients. These events result in HIV-induced immunosuppression and its subsequent sequelae, opportunistic infections and neoplasms.

In addition to CD4+ T cells, the host range of HIV includes cells of the mononuclear phagocytic lineage (Dalgleish et al., supra), including blood monocytes, tissue macrophages, Langerhans cells of the skin and dendritic reticulum cells within lymph nodes. HIV is also neurotropic, capable of infecting monocytes and macrophages in the central nervous system causing severe neurologic damage. Macrophage/monocytes are a major reservoir of HIV. They can interact and fuse with CD4-bearing T cells, causing T cell depletion and thus contributing to the pathogenesis of AIDS.

Anti-HIV Drugs

Intensive efforts are currently under way to develop therapies to prevent or intervene in the development of clinical symptoms in HIV-infected individuals. For the most part, efforts have been focused on the use of nucleoside analogue drugs such as AZT (azidothymidine), and on other dideoxynucleoside derivatives such as ddA, ddT, ddI, and ddC. These drugs inhibit the viral enzyme reverse transcriptase, thereby inhibiting de novo infection of cells. However, once viral infection has been established within a cell, viral replication utilizes host cell enzymes. Thus, drugs which inhibit only reverse transcriptase tend to have limited effects. While the spread of free virus within the organism can be blocked, the mechanisms of syncytia formation and pathogenesis through direct intercelluar spread remain. Accordingly, there is a need to provide new anti-HIV drugs which are not limited to inhibiting reverse transcription as their mechanism of action.

Various efforts are currently underway to develop therapeutic agents to arrest the replication of the human immunodeficiency virus (HIV). Although several nucleoside HIV-1 reverse transcriptase (RT) inhibitors, including AZT, ddI, ddC and D4T have been approved by the FDA and are in use clinically, all of these compounds have adverse side effects, and the HIV mutates so quickly that the virus has developed resistance to these drugs. Therefore, compounds which possess potent anti-HIV activity with different modes of action are urgently needed to add to existing anti-HIV therapies. Currently, development of new anti-HIV agents is focused on discovering different compounds which either have novel structures or new mechanisms of action.

Much effort has been expended on plant-derived natural products as new lead compounds for anti-HIV agents, as well as developing modifications of these lead compounds. Suitable structural modification of the initial lead structures may provide derivatives with greatly enhanced activity. As one example, some of the present inventors isolated and identified suksdorfin as an anti-HIV compound from *Lomatium suksdorfii*. Subsequent modification of suksdorfin yielded 3',4'-di-O-(–)-camphanoyl-(+)-cis-khellactone (DCK), which compound has demonstrated extremely potent inhibitory activity against HIV replication in H9 lymphocyte cells with an $EC_{50}$ value of 0.0004 μM and a therapeutic index (T.I.) value of 136,719.

Previously, betulinic acid and platanic acid were isolated as anti-HIV principles from *Syzigium claviflorum*.[7] Betulinc acid (1) and platanic acid (12) exhibited inhibitory activity against HIV-1 replication in H9 lymphocyte cells with $EC_{50}$ values of 1.4 μM and 6.5 μM, respectively, and T.I. values of 9.3 and 14, respectively. Hydrogenation of betulinic acid yielded dihydrobetulinic acid (6), which showed slightly more potent anti-HIV activity with an $EC_{50}$ value of 0.9 and a T.I. value of 14. Based upon these findings, modification of these lead compounds, betulinic acid and dihydrobetulinic acid, has been carried out and has led to the discovery of additional potent anti-HIV agents.

A number of triterpenoids, including betulinic acid, have several known medical applications, including use as an anticancer drug. Anderson et al., in WO 95/04526, discuss derivatives of triterpenoids which have been used in cancer therapy, including their activity against polyamines which are required by cells to grow at an optimal rate. Some of these triterpenoids have been found to interfere with the enzymatic synthesis of polyamines required for optimum cell growth, and thus inhibit the growth of cancer cells, particularly by inhibiting ornithine decarboxylase. Betulinic acid has been reported also to possess anti-inflammatory activity, which may be due to its capacity to inhibit enzymes involved in leukotriene biosynthesis, including 5-lipoxygenase.

Chan, in British patent 1,425,601, discloses that carboxylated derivatives of dihydrobetulinic acid can be included in pharmaceutical compositions, but there is no hint as to what use these compounds have.

SUMMARY OF THE INVENTION

Betulinic acid and dihydrobetulinic acid acyl derivatives according to the present invention have been found to have potent anti-HIV activity. The $C_3$-hydroxy, $C_{17}$-carboxylic acid and $C_{20}$-exomethylene groups in betulinic acid can be easily modified. It has been found that introducing a $C_2$ to $C_{20}$ substituted or unsubstituted acyl group at the $C_3$-hydroxy group of betulinic acid and dihydrobetulinic acid can be readily effective to produce the corresponding 3-O-acyl derivatives. Thus, betulinic acid and dihydrobetulinic acid were treated with 3,3-dimethylglutaric anhydride or diglycolid anhydride in pyridine in the presence of dimethylaminopyridine to produce the corresponding 3-O-acyl derivatives (4,5, 9 and 10). In contrast, similar treatment of betulinic acid and dihydrobetulinic acid with dimethylsuccinic anhydride produced a mixture of 3-O-(2',2'-dimethylsuccinyl) and 3-O-(3',3'-dimethylsuccinyl)-betulinic acid (2 and 3) and -dihydrobetulinic acid (7 and 8), respectively. The mixture was successfully separated by preparative scale HPLC yielding pure samples. The structures of these isomers were assigned by long-range $^1H$-$^{13}C$ COSY examinations.

The compounds of the present invention have the following formulae:

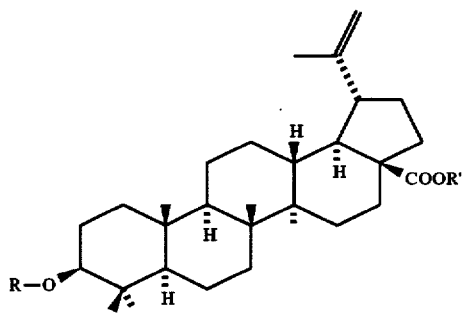

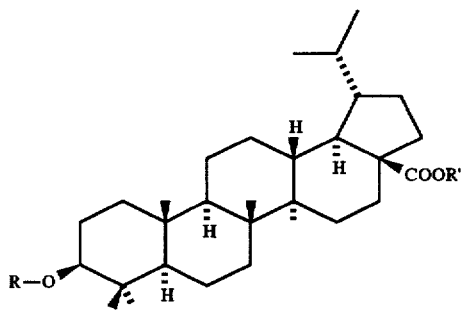

where R may be a mono- or dicarboxyacyl group, substituted or unsubstituted, of from about 2 to about 20 carbon atoms and r' may be H or a $C_2$-$C_{10}$ substituted or unsubstituted alkyl or aryl group, such as acetyl, benzyl, etc.

Of particular interest are compounds of the formula:

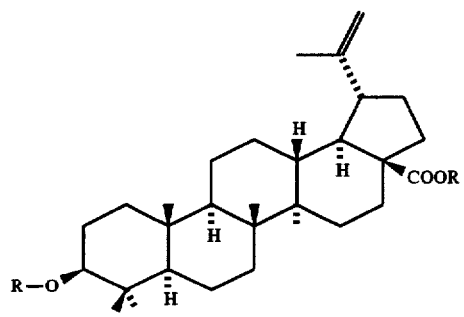

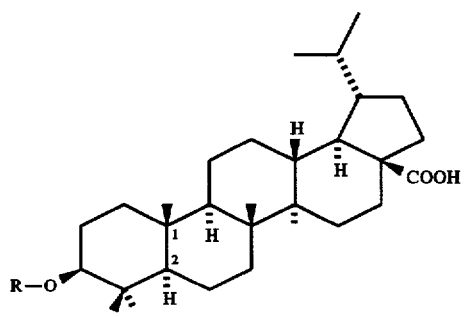

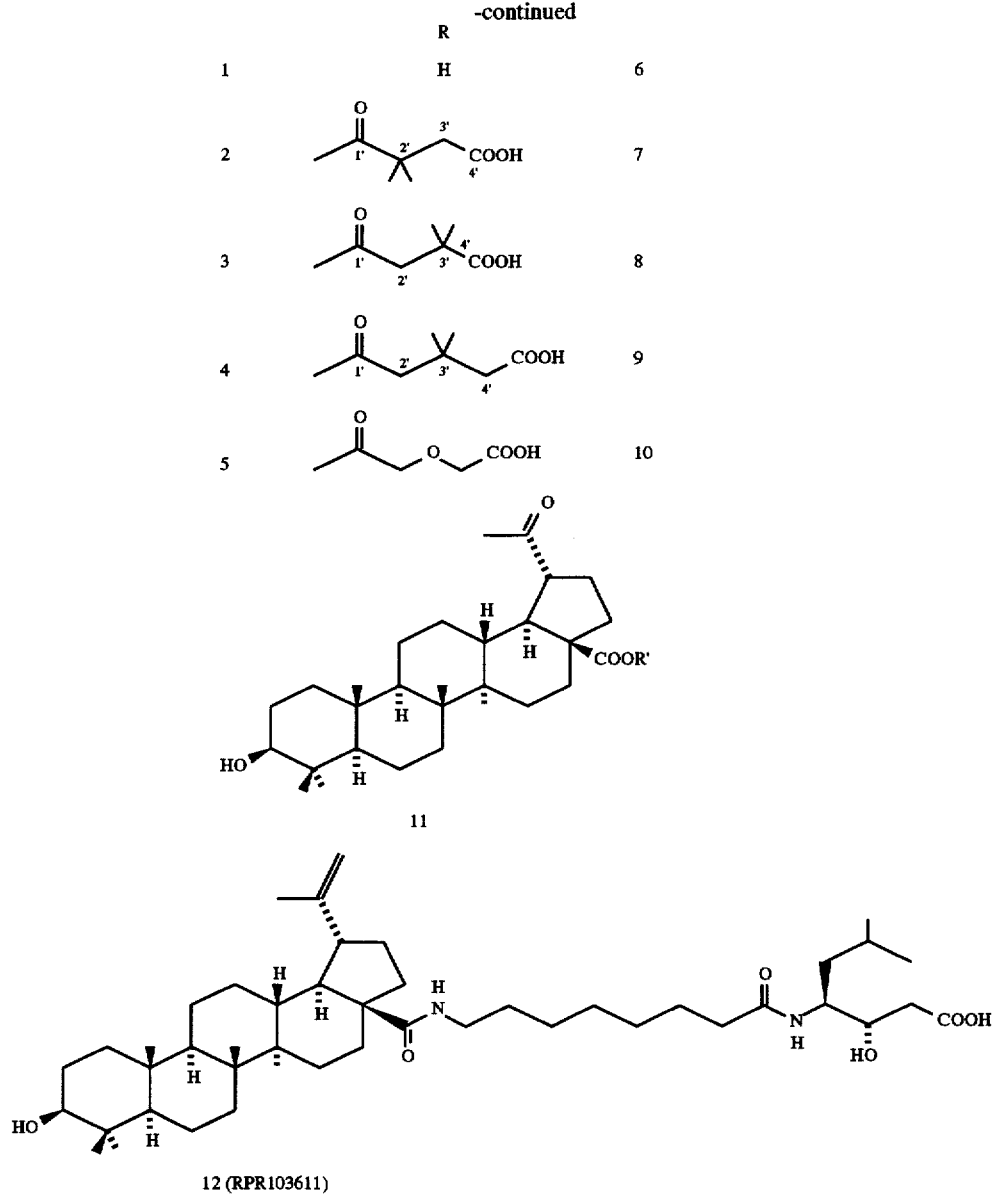

Anti-HIV assays indicated that 3-O-(3',3'-dimethylsuccinyl)-betulinic acid (3) and -dihydrobetulinic acid (8) both demonstrated extremely potent anti-HIV activity in acutely infected H9 lymphocytes with $EC_{50}$ values of less than $1.7 \times 10^{-5}$ µM, respectively. These compounds exhibited remarkable T.I. values of more than 970,000 and more than 400,000. In contrast, compounds 2 and 7, the 2',2'-dimethyl isomers, showed anti-HIV activities with $EC_{50}$ values of 2.7 and 0.56 µM, respectively, and T.I. values of 5.9 and 13.8, respectively, which were significantly lower than those of 3 and 8. Compounds, 4, 5, 9, and 10 also exhibited potent anti-HIV activities with $EC_{50}$ ranging from 0.01 to $2.3 \times 10^{-3}$ µM, and T.I. values from 1017 to 2344.

The $C_3$ acyl groups of the more active compounds have dimethyl groups or oxygen at the $C_{3'}$ position. Since the lone pairs of the oxygen in the diglycoyl group might correspond to the dimethyl groups at $C_{3'}$ in the dimethylsuccinyl or dimethylglutaryl groups, these three acyl groups are structurally similar to one another. This observation suggests that this type of acyl group might be important to the enhanced anti-HIV activity.

The inhibitory activities of 8 and 9 against HIV-1 replication in PHA-stimulated peripheral blood mononuclear cells (PBMCs) were also evaluated. These compounds also displayed potent inhibitory effects in this assay with $EC_{50}$ values of 0.00299 and 0.0292 µM, respectively, although the T.I. values for these compounds in PBMCs were lower than those in H9 cells.

As a mechanism of action study, the inhibitory activity of compounds 1–6 and 8–10 against HIV-1 reverse transcriptase was investigated. The tested compounds did not inhibit HIV reverse transcriptase activity at a concentration of 100 µg/µL. Recently, other betulinic acid derivatives, e.g., RPR103600, have been reported as anti-HIV agents.[8] They were shown to inhibit HIV-induced membrane fusion. Therefore, compounds 1–6 and 8–10 were also evaluated for inhibitory activity against HIV induced membrane fusion. Compounds 2–5 and 8–10 inhibited syncytia formation in a concentration range of 20–40 µg/mL, suggesting than an inhibitory effect against HIV induced membrane fusion could be involved in their mechanisms of action. However, the anti-HIV activity of compound 3 is 540,000 times greater than that of compound 2, although these compounds inhibited syncytia formation at the same concentration. Compound RPR103611 was reported to inhibit syncytia formation at 3 µg/mL and for this purpose was approximately ten times more potent than compounds 2–5 or 8–10 in this assay. However, the cell line used in assaying the compounds of the present invention, CEM4, was different from the cell line used in the literature, H9. The anti-HIV activities of compounds 3 and 8 in H9 cells and PMBCs were about 10 to 1000 times greater than those of RPR103611 reported in the literature. This observation indicated that at least one other mechanism of action other than inhibition of syncytia formation could be involved in the anti-HIV activity shown by these compounds.

The invention is also directed to a method for treating a subject infected with HIV-1 by administering at least one of the above-noted betulinic acid derivatives, optionally in combination with any one or more of the known anti-AIDS therapeutics or an immunostimulant.

The treatment methods of the present invention also include administering to a subject infected with HIV-1 a conjugate of a betulinic acid derivative as described above with soluble CD4, CD4 derivatives, antibodies specific for CD4, or HIV-coded glycoproteins such as gp120 and gp41, or antibodies thereto.

Other features, advantages, embodiments, aspects and objects of the present invention will be clear to those skilled in the areas of relevant art, based upon the description, teaching and guidance presented herein.

The compounds of the present invention have been unexpectedly discovered to have anti-retroviral activity, thus providing suitable compounds and compositions for treating retroviral infections, optionally with additional pharmaceutically active ingredients, such as anti-retroviral, anti-HIV, and/or immuno-stimulating compounds or antiviral antibodies or fragments thereof.

By the term "anti-retroviral activity" or "anti-HIV activity" is intended the ability to inhibit at least one of:

(1) retroviral attachment to cells;

(2) viral entry into cells;

(3) cellular metabolism which permits viral replication;

(4) inhibition or intercellular spread of the virus;

(5) synthesis and/or cellular expression of viral antigens;

(6) activity of virus-coded enzymes (such as reverse transcriptase and protease); and/or (7) any known retroviral or HIV pathogenic actions, such as, for example, immunosuppression. Thus, any activity which tends to inhibit any of these mechanisms is "anti-retroviral activity" or "anti-HIV activity."

DETAILED DESCRIPTION OF THE INVENTION

A betulinic acid or dihydrobetulinic acid derivative of the present invention can be used for treatment of retroviral (e.,g., HIV) infection either alone, or in combination with other modes of therapy known in the art. Such modes of therapy can include chemotherapy with drugs, such as, but not limited to, at least one of AZT, ddC, ddA, ddT, ddI, or any other anti-retroviral drugs or antibodies in combination with each other, or associated with a biologically based therapeutic, such as, for example, soluble CD4, antibodies to CD4, and conjugates of CD4 or anti-CD4, or as additionally presented herein.

Because the betulinic acid or dihydrobetulinic acid derivatives of the present invention are relatively less or substantially non-toxic to normal cells, their utility is not limited to the treatment of established retroviral infections. For example, a betulinic acid derivative according to the present invention can be used in treating blood products, such as those maintained in blood banks. The nation's blood supply is currently tested for antibodies to HIV. However, the test is still imperfect and samples which yield negative tests can still contain HIV virus. Treating the blood and blood products with the betulinic acid derivatives of the present invention can add an extra margin of safety by killing any retrovirus that may have gone undetected.

Pharmaceutical Compositions

Pharmaceutical compositions of the present invention can comprise at least one of the betulinic acid or dihydrobetulinic derivatives. Pharmaceutical compositions according to the present invention can also further comprise other antiviral agents such as, but not limited to, AZT, ddI, 2'-β-fluoro-ddI, ddA, ddG, ddC, 2'-β-fluoro-ddC, d4T, AzddU, phosphonylmethoxyethyl-adenine, or soluble CD4, or immunomodulators, e.g., as presented below. For a review of therapeutic agents in HIV infections, see, e.g., Mitsuya et al., FASEB J. 5:2369–2381, 1991, which reference is hereby incorporated by reference.

Additional suitable antiviral agents for optimal use with a betulinic acid derivative of the present invention can include, but are not limited to, AL-721 (lipid mixture) manufactured by Ethigen Corporation and Matrix Research laboratories; Amphotericin B methyl ester; Ampligen (mismatched RNA) developed by DuPont/HEM Research; anti-AIDS antibody (Nisshon Food) 1 AS-101 (heavy metal based immunostimulant); AZT (azidothymidine/Retrovir/Zidovudine), manufactured by Burroughs Wellcome; Betaseron (β-interferon) manufactured by Triton Biosciences (Shell oil); butylated hydroxytoluene; Carrosyn (polymannoacetate) Castanospermine; Contracan (stearic acid derivative); Creme Pharmatex (containing benzalkonium chloride) manufactured by Pharmalec; CS-87 (5-unsubstituted derivative of Zidovudine), Cytovene (ganciclovir) manufactured by Syntex Corporation; ddC (dideoxycytidine) manufactured by Hoffmann-LaRoche and other nucleoside analogues; dextran sulfate; D-penicillamine (3-mercapto-D-valine) manufactured by Carter-Wallis and Degussa Pharmaceutical; Foscarnet (trisodium phosphonoformate) manufactured by Astra AB, fusidic acid manufactured by Leo Lovens' glycyrrhizin (a constituent of licorice root); HPA-23 (ammonium-21-tungsto-9-antimonate) manufactured by Rhone-Poulenc Santé; human immunevirus antiviral developed by Porton Products International; Ornidyl (eflornithine) manufactured by Merrell-Dow; nonoxinol; pentamidine isethionate (PENTAM-300) manufactured by Lypho Med; Peptide T (octapeptide sequence) manufactured by Peninsula Laboratories; Phenytoin (Warner-Lambert); Ribavirin; Rifabutin (ansamycin) manufactured by Adria Laboratories; rsT4 (recombinant soluble T4) manufactured by Biogen, Genentech and Smith, Kline Beecham; Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; Wellferon (α-interferon) manufactured by Burroughs Wellcome; Zovirex (acyclovir, AZT) manufactured by Burroughs Wellcome.

Pharmaceutical compositions of the present invention can also further comprise immunomodulators. Suitable immunomodulators for optional use with a betulinic acid derivative of the present invention in accordance with the present invention can include, but are not limited to: ABPP (Bropririmine); Ampligen (mismatched RNA) DuPont/HEM Research; anti-human interferon-α-antibody (Advance Biotherapy and Concepts)' anti-AIDS antibody (Nisshon Food), AS-101 (heavy metal based immunostimulate; ascorbic acid and derivatives thereof; interferon-β; Carrosyn (polymannoacetate); Ciamexon (Boehringer-Mannheim); cyclosporin; cimetidine; CL-246,738 (American Cyanamide); colony stimulating factors, including GM-CSF (Sandoz, Genetics Institute); dinitrochlorobenzene; interferon-α; inteferon-gamma; glucan; hyperimmune gamma-globulin (Bayer); IMREG-1 (leukocyte dialyzate) and IMREG-2 (IMREG Corp.); immuthiol (sodium diethylthiocarbamate) (Institut Merieux); interleukin-1 or interleukin-1 (Cetus Corporation; Hoffmann-LaRoche; Immunex); isoprinosine (inosine pranobex); Krestin (Sankyo); LC-9018 (Yakult); lentinan (Ajinomoto/Yamanouchi); LF-1695 (Fournier); methionine-enkephalin (TNI Pharmaceuticals; Sigma Chemicals); Minophagen C; muramyl tripeptide, MTP-PE (Ciba-Geigy); naltrexone ("Trexan" DuPont); Neutropin. RNA immunomodulator (Nippon Shingaku); shosaikoto and ginseng; thymic humoral factor; TP-05 (Thymopentin, Ortho Pharmaceuticals); Thymosin factor 5 and Thymosin 1; Thymostimulin; TNF (Tumor necrosis factor) manufactured by Genentech; and vitamin B preparations.

The preferred animal subject of the present invention is a mammal. By the term "mammal" is meant an individual belonging to the class Mammalia. The invention is particularly useful in the treatment of human patients.

The term "treating" means the administering to subjects a betulinic acid or dihydrobetulinic acid derivative for purposes which can include prevention, amelioration, or cure of a retroviral-related pathology.

Medicaments are considered to be provided "in combination" with one another if they are provided to the patient concurrently or if the time between the administration of each medicament is such as to permit an overlap of biological activity.

In one preferred embodiment, at least one betulinic acid or dihydrobetulinic acid derivative comprises a single pharmaceutical composition.

Pharmaceutical compositions for administration according to the present invention can comprise at least one betulinic acid or dihydrobetulinic acid derivative according to the present invention in a pharmaceutically acceptable form optionally combined with a pharmaceutically acceptable carrier. These compositions can be administered by any means that achieve their intended purposes. Amounts and regimens for the administration of a betulinic acid derivative according to the present invention can be determined readily by those with ordinary skill in the clinical art of treating a retroviral pathology.

For example, administration can be by parenteral, such as subcutaneous, intravenous, intramuscular, intraperitoneal, transdermal, or buccal routes. Alternatively, or concurrently, administration can be by the oral route. The dosage administered depends upon the age, health and weight of the recipient, type of previous or concurrent treatment, if any, frequency of treatment, and the nature of the effect desired.

Compositions within the scope of this invention include all compositions comprising at least one betulinic acid or dihydrobetulinic acid derivative according to the present invention in an amount effective to achieve its intended purpose. While individual needs vary, determination of optimal ranges of effective amounts of each component is within the skill of the art. Typical dosages comprise about 0.1 to about 100 mg/kg body weight. The preferred dosages comprise about 1 to about 100 mg/kg body weight of the active ingredient. The most preferred dosages comprise about 10 to about 100 mg/kg body weight.

Therapeutic administration can also include prior, concurrent, subsequent or adjunctive administration of at least one additional betulinic acid or dihydrobetulinic acid derivative according to the present invention or other therapeutic agent, such as an anti-viral or immune stimulating agent. In such an approach, the dosage of the second drug can preferably be the same as or different from the dosage of the first therapeutic agent. Preferably, the drugs are administered on alternate days in the recommended amounts of each drug.

Administration of a compound of the present invention can also optionally include previous, concurrent, subsequent or adjunctive therapy using immune system boosters or immunomodulators. In addition to the pharmacologically active compounds, a pharmaceutical composition of the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

Pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharide, for example, lactose or sucrose, mannitol or sorbitol; cellulose preparations and/or calcium phosphates, such as tricalcium phosphate or calcium hydrogen phosphate; as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers can be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions can be administered. Suitable lipophilic solvents or vehicles include fatty oils, such as sesame oil, or synthetic fatty acid esters, such as ethyl oleate or triglycerides. Aqueous injection suspensions that can contain substances which increase the viscosity of the suspension include, for example, sodium carboxymethyl cellulose, sorbitol, and/or dextran. Optionally, the suspension can also contain stabilizers.

A pharmaceutical formulation for systemic administration according to the invention can be formulated for enteral, parenteral or topical administration. Indeed, all three types of formulation can be used simultaneously to achieve systemic administration of the active ingredient.

Suitable formulations for oral administration include hard or soft gelatin capsules, dragees, pills, tablets, including coated tables, elixirs, suspensions, syrups or inhalations and controlled release forms thereof.

Solid dosage forms in addition to those formulated for oral administration include rectal suppositories.

The betulinic acid or dihydrobetulinic acid derivatives of the present invention can also be administered in the form of an implant when compounded with a biodegradable slow-release carrier. Alternatively, the betulinic acid or dihydrobetulinic acid derivatives of the present invention can be formulated as a transdermal patch for continuous release of the active ingredient.

Suitable formulations for topical administration include creams, gels, jellies, mucilages, pastes and ointments. Suitable injectable solutions include intravenous subcutaneous and intramuscular injectable solutions. Alternatively, the betulinic acid or dihydrobetulinic acid derivatives may be administered in the form of an infusion solution or as a nasal inhalation or spray.

Having now generally described the invention, the same will be more readily understood through reference to the following:

The derivatives of betulinic acid and dihydrobetulinic acid of the present invention were all synthesized by refluxing a solution of betulinic acid (1) or dihydrobetulinic acid (6), dimethylaminopyridine (1 equivalent mol), and an appropriate anhydride (2.5–10 equivalent mol) in anhydrous pyridine (5–10 mL). The reaction mixture was then diluted with ice water and extracted with $CHCl_3$. The organic layer was washed with water, dried over $MgSO_4$, and concentrated under reduced pressure. The residue was chromatographed using silica gel column or semi-preparative-scale HPLC to yield the product.

Preparation of 3-O-(2',2'-dimethylsuccinyl)betulinic acid (2):

3-O-(2',2'-dimethylsuccinyl)betulinic acid (2) was prepared as above using a solution of betulinic acid, dimethylaminopyridine, and dimethylsuccinic anhydride in anhydrous pyridine. The yield was 3.1%. Crystallization form methanol gave colorless needles, melting point 279°–280° C.; $[\alpha]_D^{19}$+36.2° [c=0.35, CHCl3-MeOH (1:1)]; positive FABMS m/z 585 (M+H)$^+$; Negative FABMS m/z 583 (M−H)$^−$; HR-FABMS calculated for $C_{36}H_{57}O_6$ 585.4155, found m/z 585.4156; $^1$H NMR (pyridine-$d_5$): 0.75, 0.93, 1.03 (×2), 1.06 (each 3H, s; 4-$(CH_3)_2$, 8-$CH_3$, 10-$CH_3$, 14-$CH_3$), 1.49 (6H, 2, 2'-$CH_3$×2), 1.80 (3H, s, 20-$CH_3$), 2.94 (2H, s, H2-3'), 3.55 (1H, m, H-19), 4.77 (1H, dd, J=5, 11.5 Hz, H-3), 4.79, 4.95 (each 1H, br s, H-30).

3-O-(3',3'-dimethylsuccinyl)-betulinic acid (3): yield 70% (starting with 542 mg of 1); crystallization from MeOH gave colorless needles; mp 274°–276° C.; $[\alpha]_D^{19}$+23.5° (c=0.71), $CHCl_3$-MeOH[1:1]); Positive FABMS m/z 585 (M+H)$^+$; Negative FABMS m/z 583 (M−H)$^−$; HR-FABMS calcd for $C_{36}H_{57}O_6$ 585.4155, found m/z 585.4161; $^1$H NMR (pyridine-d5): 0.73, 0.92, 0.97, 1.01, 1.05 (each 3H, s; 4-$(CH_3)_2$, 8-$CH_3$, 10-$CH_3$, 14-$CH_3$), 1.55 (6H, s, 3'-$CH_3$×2), 1.80 (3H, s, 20-$CH_3$), 2.89, 2.97 (each 1H, d, J=15.5 Hz, H-2'), 3.53 (1H, m, H-19), 4.76 (1H, dd, J=5.0, 11.5 Hz, H-3), 4.78, 4.95 (each 1H, br s, H-30).

3-O-(3',3'-dimethylglutaryl)-betulinic acid (4): yield 59.5% (starting with 51.3 mg of 2); crystallization from MeOH-$H_2O$ gave colorless needles; mp 214°–215° C.; $[\alpha]_D^{20}$+9.8° (c=1.2, $CHCl_3$-MeOH[1:1]); $^1$H-NMR (pyridine-$d_5$): 0.77, 0.91, 0.95, 1.03, 1.07, 1.80 (each 3H, s; 4-$(CH_3)_2$, 8-$CH_3$, 10-$CH_3$, 14-$CH_3$, 20-$CH_3$), 4.73 (1H, dd, J=4.5, 11.5 Hz, H-3), 4.78, 4.95 (each 1H, br.s; H-30). Anal. Calcd for $C_{37}H_{58}O_6$·4$H_2O$: C 66.24, H 9.92; found C 65.91, H 9.76.

3-O-diglycolyl-betulinic acid (5): yield 84.7% (starting with 49.6 mg of 1); an amorphous powder; $[\alpha]_D^{20}$+2.1° (c=1.1, $CHCl_3$-MeOH[1:1]); $^1$H-NMR (methanol-$d_4$-$CDCl_3$ [1:1]): 0.85, 0.88 (×2), 0.97, 1.00 (each 3H, s; 4-$(CH_3)_2$, 8-$CH_3$, 10-$CH_3$, 14-$CH_3$), 1.69 (20-$CH_3$), 4.21, 4.23 (each 2H, s; $H_2$-2' and 4'), 4.65–475 (1H, br s, H-3), 4.60, 4.73 (each 1H, br s, H-30). Anal. Calcd for $C_{34}H_{52}O_7$·$H_2O$: C 69.12, H 9.21; found C 69.60, H 9.03.

3-O-(2',2'-dimethylsuccinyl)-dihydrobetulinic acid (7): yield 4.8% (starting with 155.9 mg of 6); crystallization from MeOH-$H_2O$ gave colorless needles; mp 297°–298° C.; $[\alpha]_D^{17}$−32.2° (c=0.21, $CHCl_3$-MeOH[1:1]); Positive FABMS m/z 587 (M+H)$^+$; Negative FABMS m/z 585 (M−H)$^−$; HR-FABMS calcd for $C_{36}H_{59}O_6$587.4311, found m/z 587.4308; $^1$H NMR (pyridine-$d_5$): 0.85, 0.94 (each 3H, d, J=6.5 Hz; 20-$(CH_3)_2$, 0.77, 0.94, 1.03 (×2), 1.04 (each 3H, s; 4-$(CH_3)_2$, 8-$CH_3$, 10-$CH_3$, 14-$CH_3$), 1.50 (6H, s, 2'-$CH_3$× 2), 2.95 (2H, s, $H_2$-3'), 4.79 (1H, dd, J=4.5, 11.5 Hz; H-3).

3-O-(3',3'-dimethylsuccinyl)-dihydrobetulinic acid (8): yield 24.5% (starting with 155.9 mg of 6); crystallization from MeOH-$H_2O$ gave colorless needles; mp 291°–292° C.; $[\alpha]_D^{20}$−13.4° (c=1.1, $CHCl_3$-MeOH[1:1], $^1$H NMR (pyridine-d₅): 0.85, 0.94 (each 3H, d, J=7.0 Hz; 20-(CH₃)₂), 0.75, 0.93, 0.97, 1.01, 1.03 (each 3H, s; 4-(CH₃)₂, 8-CH₃, 10-CH₃, 14-CH₃), 1.55 (6H, s; 3'-CH₃×2), 2.89, 2.97 (each 1H, d, J=15.5 Hz; H-2'), 4.77 (1H, dd, J=5.0, 11.0 Hz, H-3); Anal. Calcd for $C_{36}H_{58}O_6 \cdot 5/2H_2O$: C 68.43, H 10.04; found C 68.64, H 9.78.

3-O-(3',3'-dimethylglutaryl)-dihydrobetulinic acid (9): yield 93.3% (starting with 100.5 mg of 6); crystallization from needles MeOH-H₂O gave colorless needles; mp 287°–289° C.; $[\alpha]_D^{20}$ –17.9° (c=0.5, CHCl₃-MeOH[1:1]); ¹H-NMR (pyridine-d₅): 0.86, 0.93 (each 3H, d, J=6.5 Hz; 20-(CH₃)₂), 0.78, 0.92, 0.96, 1.02, 1.05 (each 3H, s; 4-(CH₃)₂, 8-CH₃, 10-CH₃, 14-CH₃), 1.38, 1.39 (each 3H, s; 3'-CH₃× 2), 2.78 (4H, m, H₂-2' and 4'), 4.76 (1H, dd, J=4.5, 11.5 Hz; H-3). Anal. Calcd for $C_{37}H_{60}O_6$: C 73.96, H 10.06; found C 73.83, H 10.10.

3-O-diglycolyl-dihydrobetulinic acid (10): yield 79.2% (starting with 103.5 mg of 6); an off-white amorphous powder; $[\alpha]_D^{20}$–9.8° (c=1.1, CHCl₃-MeOH[1:1]); ¹H-NMR (pyridine-d₅): 0.79, 0.87 (each 3H, d, J=6.5 Hz; 20-(CH₃)₂), 0.87, 0.88, 0.91, 0.98, 1.01 (each 3H, s; 4-(CH₃)₂, 8-CH₃, 10-CH₃, 14-CH₃), 4.21, 4.23 (each 2H, s, H₂-2' and 4'), 4.57 (1H, dd, J=6.5, 10.0 Hz, H-3); Anal. Calcd for $C_{34}H_{54}O_7 \cdot 2H_2O$: C 66.85, H 9.57; found C 67.21, H 9.33.

Anti-HIV Assays

The T cell line, H9, and the promonocytic cell line, U937, were maintained separately in continuous culture with complete medium (RPMI 1640 with 10% fetal calf serum) at 5% CO2 and 37° C. The cell lines were used in experiments only when in the logarithmic phase of growth, whereas uninfected peripheral blood mononuclear cells (PBMCs) were first stimulated with PHA (1 µg/mL) for three days. All cell targets were incubated with HIV-1 (IIIB isolate, $TCID_{50}$ $10^4$ IU/ml, at a multiplicity of infection of 0.01–0.01 IU/cell) for one hour at 37° C. and 5% CO2. The cell lines and PBMCs were washed thoroughly to remove unadsorbed virions and resuspended at $4 \times 10^5$ cells/ml in complete medium or complete medium with 10% v/v interleukin 2 (IL-2), respectively. One ml. aliquots were placed into wells of 24-well culture plates containing an equal volume of test compounds (diluted in the appropriate culture medium). The toxicity of each compound was assessed by determining the number of compound-exposed uninfected cells that remained after four days at 37° C. and 5% CO2. A p24 antigen ELISA assay was used to determine the level of virus released in the medium of the HIV-infected cultures. The p24 antigen assay used a HIV-1 anti-p24 specific monoclonal antibody as the capture antibody coated onto 96-well plates. Following a sample incubation period, rabbit serum containing antibodies for HIV-1 p24 was used to tag any p24 "captured: onto the microtiter well surface. Peroxidase conjugated goat anti-rabbit serum was then used to tag HIV-1 p24 specific rabbit antibodies that had complexed with captured p24. The presence of p24 in test samples was then revealed by addition of substrate. The cutoff for the p24 ELISA assay was 12.5 pg/ml. P24 in the culture medium was quantitated against a standard curve containing known amounts of p24. The effective ($EC_{50}$) and inhibitory ($IC_{50}$) concentrations for anti-HIV activity and cytotoxicity, respectively, were determined.

HIV-1 Reverse Transcriptase Assay

HIV-1 reverse transcriptase microassay was adapted from techniques described by Goff et al., *J. Virol.*, 1981, 38, 239–248 and Willey et al., *J. Virol.*, 1988, 62, 139–147.

Ten microliters of virion associated HIV-1 IIIB reverse transcriptase in 1% Triton X-100 was mixed with 50 microliters of a reaction cocktail containing 50 mM Tri-HCl (pH 7.8), 75 mM KCl, 2 mM dithiothreitol, 5 mM $MgCl_2$, 5 mg/ml poly (A) [Pharmacia], 0.25 unit/ml oligo(dT) [Pharmacia]; 0.05% Nonidet P40 and 10 mCi/ml $^{32}$P-dTTP in the presence of various concentrations of test compound. After incubating for one hour at 37° C., 40 microliters of the reaction mixture was applied to a Schleicher & Schuell NA 45 membrane saturated with sxSSC (0.3M NaCl, 30 mM sodium citrate, pH 7.0) in a Schleicher & Schuell Minifold over one sheet of GB003 filter paper. Each well of the minifold was washed four times with 2×SSC. Autoradiography was performed, and radioactivity was quantified with a Packard Matrix (Meriden, Conn.) 9600 direct beta counter.

Cell Fusion Assay

Cell fusions were performed as described in Matthews et al., *Proc. Natl. Acad. Sci. USA*, 1987, 84, 5424–5428. MOLT-4 cells ($7 \times 10^4$) were incubated with HIV-$1_{LAI}$ chronically infected CEM cells ($10^4$) in 96-well half-area flat-bottomed plates (Costar) in 100 microliters culture medium were incubated with the cell mixtures at 37° C. for 24 hours. Multinucleated syncytia were enumerated by microscopic examination of the entire contents of each well.

The results of the above tests are shown in Table 1.

TABLE 1

Anti-HIV, HIV-RT, and Fusion Assay for Betulinic Acid and Dihydrobetulinic Acid Derivatives

| Compounds | $EC_{50}$ (µM)[a] | T.I. | HIV-RT Assay $IC_{50}$ (µg/mL)[b] | Fusion Assay $IC_{100}$ (µg/mL)[c] |
|---|---|---|---|---|
| 1 | 1.4 | 9.3 | >100 | >100 |
| 2 | 2.7 | 5.9 | >100 | 20[d] |
| 3 | $3.5 \times 10^{-4} - 1 \times 10^{-5}$ | 20,000–700,000 | >100 | 20[d] |
| 4 | $2.3 \times 10^{-3}$ | 1,974.0 | >100 | 30[d] |
| 5 | 0.01 | 1,172.0 | >100 | 40[e] |
| 6 | 0.9 | 14.0 | >100 | >100 |
| 7 | 0.56 | 13.8 | N.T.[g] | N.T.[g] |
| 8 | $3.5 \times 10^{-4} - 5 \times 10^{-5}$ | 14,000–98,000 | >100 | 20[f] |

TABLE 1-continued

Anti-HIV, HIV-RT, and Fusion Assay for
Betulinic Acid and Dihydrobetulinic Acid Derivatives

| Compounds | EC$_{50}$ (μM)[a] | T.I. | HIV-RT Assay IC$_{50}$ (μg/mL)[b] | Fusion Assay IC$_{100}$ (μg/mL)[c] |
|---|---|---|---|---|
| 9 | 5.7 × 10$^{-3}$ | 1,017.0 | >100 | 20[f] |
| 10 | 5.6 × 10$^{-3}$ | 2,344.0 | >100 | 40[e] |
| 12 | 0.03[h] | >90[h] | No Inhibition[h] | 3[h] |

[a]Concentration which inhibits viral replication in H9 cells by 50%
[b]Concentration required to inhibit 50% of HIV-1 RT activity
[c]Concentration required to completely inhibit HIV-1 induced syncytia mediated by CEM4
[d]No noticeable cytotoxicity at 100 μg/mL
[e]Toxic to the cells at 80 μg/mL in one-day fusion assay
[f]Toxic at 40 μg/mL under the assay conditions
[g]N.T. = Not Tested
[h]Data from reference 8

Additional tests were conducted on several compounds according to the present invention for inhibition of HIV-1 replication in H9 lymphocytes and PBMCs. These results are shown in Table 2.

TABLE 2

Inhibition of HIV-1 Replication in H9 Lymphocytes and PBMCs

| Compound | Cell | EC$_{50}$ (mg/mL) | TI$_{50}$ |
|---|---|---|---|
| 8 | H9 | 0.0032 | 17,188 |
| 8 | PBMCs | 0.00175 | 2,286 |
| 8 | H9 | 0.00128 | 3,125 |
| 3 | PBMCs | 0.0175 | 229 |
| 10 | H9 | 0.0032 | 2,344 |
| 5 | H9 | 0.01 | 1,500 |

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

What is claimed is:

1. A compound of the formula:

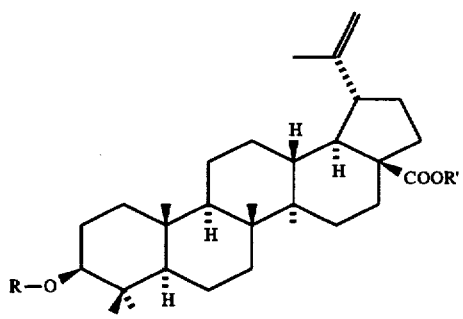

or a pharmaceutically acceptable salt or ester thereof; wherein

R is selected from the group consisting of

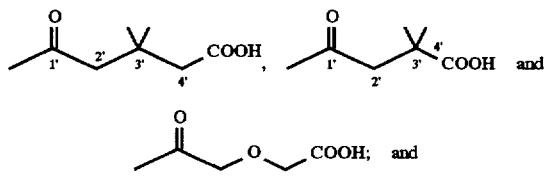

R' is one of hydrogen, C$_2$–C$_{10}$ substituted or unsubstituted alkyl, or aryl.

2. A compound of claim 1, wherein R' is one of hydrogen, acetyl or benzyl.

3. A compound of claim 1, which is one of:

3-O-(3',3'-dimethylsuccinyl)betulinic acid;
3-O-(3',3'-dimethylglutaryl)betulinic acid; or
3-O-diglycolylbetulinic acid.

4. A compound of the formula:

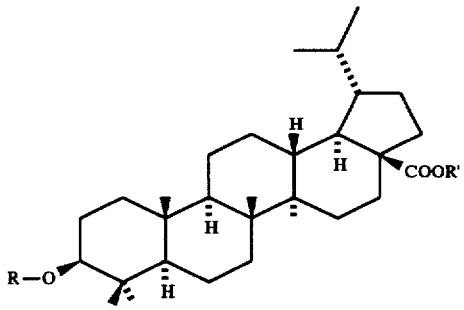

or a pharmaceutically acceptable salt or ester thereof; wherein

R is selected from the group consisting of:

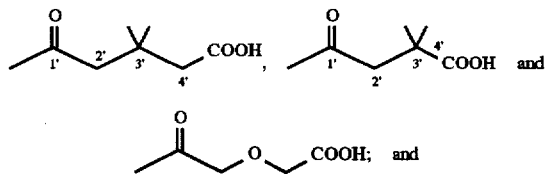

R' is hydrogen, C$_2$–C$_{10}$ substituted or unsubstituted alkyl, or aryl.

5. A compound of claim 4, wherein R' is one of hydrogen, acetyl or benzyl.

6. A compound of claim 4, which is one of:
3-O-(3',3'-dimethylsuccinyl)dihydrobetulinic acid;
3-O-(3',3'-dimethylglutaryl)dihydrobetulinic acid; or
3-O-diglycolyldihydrobetulinic acid.

7. A pharmaceutical composition comprising a compound according to claim 1 or a pharmaceutically acceptable ester, salt, ether, sulfate, or glucuronide thereof, and a pharmaceutically acceptable carrier.

8. A pharmaceutical composition according to claim 7 further comprising a drug selected from an anti-viral agent or an imunostimulating agent.

9. A pharmaceutical composition according to claim 8, wherein said antiviral agent is selected from the group consisting of gamma globulin, amantadine, guanidine, hydroxybenzimidazole, interferon-$\alpha$, interferon-$\beta$, interferon-$\gamma$, thiosemicarbazones, methisazone, rifampin, ribavirin, pyrimidine analogs, purine analogs, foscarnet, phosphonoacetic acid, acyclovir, dideoxynucleosides, and gancyclovir.

10. A pharmaceutical composition comprising a compound according to claim 4 or a pharmaceutically acceptable ester, salt, ether, sulfate, or glucuronide thereof, and a pharmaceutically acceptable carrier.

11. A pharmaceutical composition according to claim 10 further comprising a drug selected from an anti-viral agent or an imunostimulating agent.

12. A pharmaceutical composition according to claim 11, wherein said antiviral agent is selected from the group consisting of gamma globulin, amantadine, guanidine, hydroxybenzimidazole, interferon-$\alpha$, interferon-$\beta$, interferon-$\gamma$, thiosemicarbazones, methisazone, rifampin, ribavirin, pyrimidine analogs, purine analogs, foscarnet, phosphonoacetic acid, acyclovir, dideoxynucleosides, and gancyclovir.

* * * * *